United States Patent [19]

DeVries

[11] Patent Number: 4,796,626

[45] Date of Patent: Jan. 10, 1989

[54] TOURNIQUET TUBE

[75] Inventor: James H. DeVries, Grand Rapids, Mich.

[73] Assignee: DLP Inc., Grand Rapids, Mich.

[21] Appl. No.: 38,721

[22] Filed: Apr. 15, 1987

[51] Int. Cl.$^4$ ............................................. A61B 17/04
[52] U.S. Cl. ................................ 128/334 R; 128/326
[58] Field of Search ..................... 128/327, 326, 334 R

[56] References Cited

U.S. PATENT DOCUMENTS 3,476,115 11/1969 Graeff et al. ........................ 128/326
3,786,816 1/1974 Wolvek ............................ 128/326 X
3,877,434 4/1975 Ferguson et al. ................... 128/327

Primary Examiner—Michael H. Thaler
Attorney, Agent, or Firm—Barnes, Kisselle, Raisch, Choate, Whittemore & Hulbert

[57] ABSTRACT

A suture lumen for securing sutures in surgical procedures which includes a lumen with a head portion at one end of said lumen having a side projection about which suture ends may be wound to secure the ends. A notch or notches in the head portion adjacent the projection are provided to receive the free ends of the suture to prevent release until surgery is completed.

7 Claims, 2 Drawing Sheets

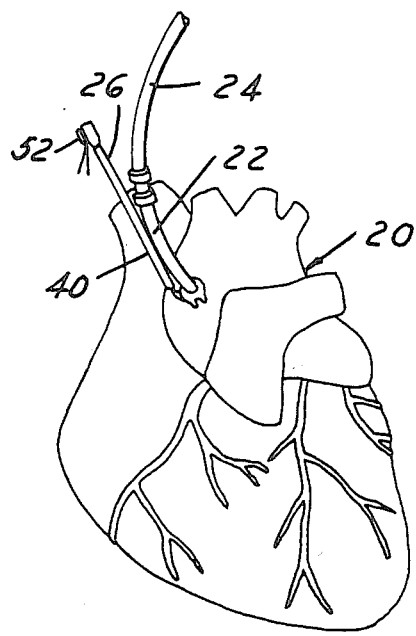
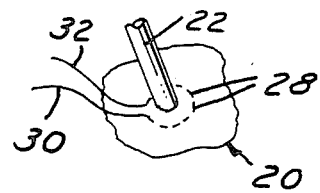
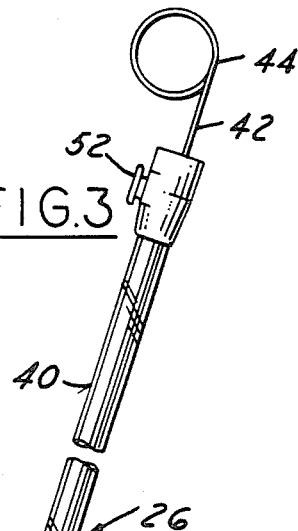
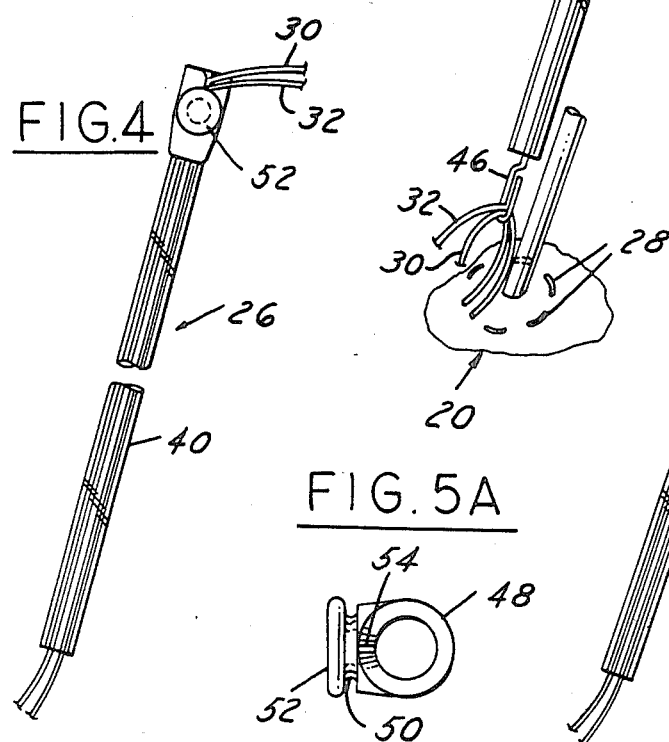
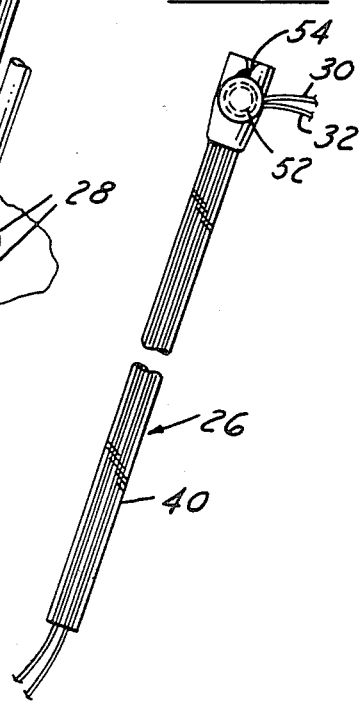
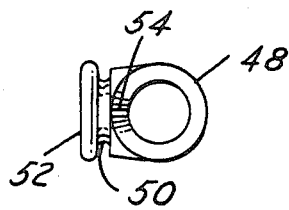

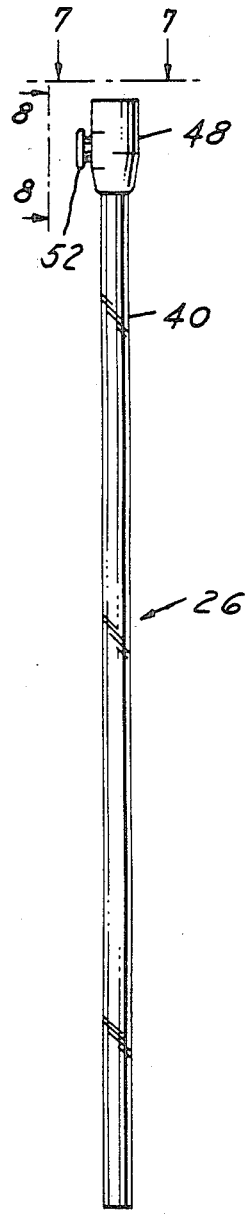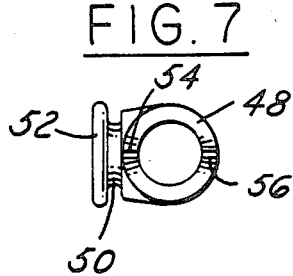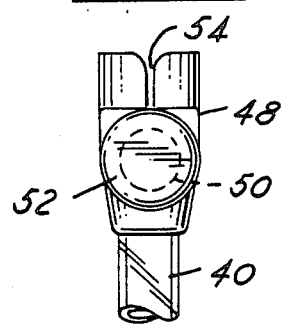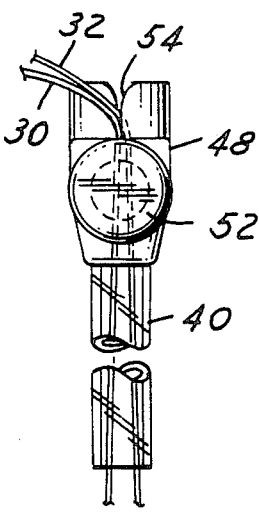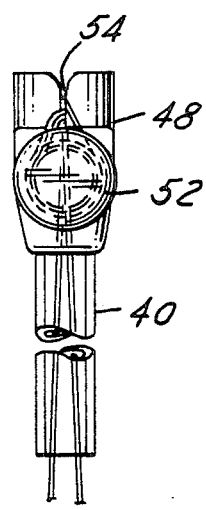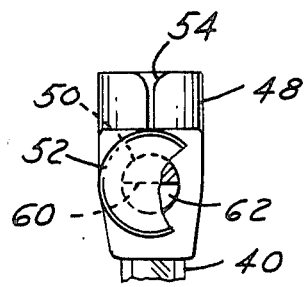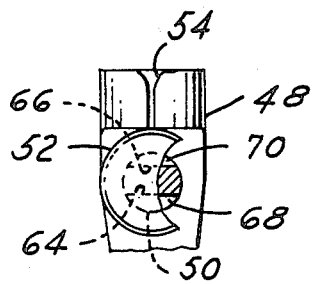

TOURNIQUET TUBE

FIELD OF INVENTION

Placement of ligature and aortic root cannula in open heart surgery.

BACKGROUND AND OBJECTS OF THE INVENTION

In the performance of open heart vascular surgery, it is a common practice to provide what is termed a purse string suture around the locus of the cannulation site which involves a series of loops of a suture around the site such that when the ends are ultimately pulled taut, the cannula aperture will be closed.

However, in the meantime a cannulazation must be accomplished and a cannula secured in place in the vessel. The cannula is used for infusing or removing fluids during surgery. During this period, the ends of the sutures must be drawn tight to hold the vessel around the cannula securely until the surgery is completed. The cannula is then removed and the purse string is pulled taut and tied in order to close the opening.

It is an object of the present invention to provide a tourniquet tube which can be used to secure the suture ends in rapid fashion and to release the ends for drawing the purse string taut.

It is a further object to provide a tourniquet tube which is a one-piece unit with no need for the application of a securing plug or hemostat to the ends of the suture.

Other objects and features of the invention will be set forth in the following description and claims in which the principles of the invention are set forth together with details to enable persons skilled in the art to practice the invention, all in connection with the best mode presently contemplated for the invention.

BRIEF DESCRIPTION OF THE DRAWINGS

DRAWINGS accompany the disclosure and the various views thereof may be briefly described as:

FIG. 1, a view of a heart organ with cannula and tourniquet tube in place.

FIG. 2, a view of a heart organ with a purse string suture in place.

FIG. 3, a view of a tourniquet tube.

FIG. 4, a side view of a tourniquet tube before securing the suture ends.

FIG. 5, a view similar to FIG. 4 after securing the sutures.

FIG. 5A, an end view of the tourniquet tube.

FIG. 6, an elevation of the tourniquet tube.

FIG. 7, an end view of the tube at line 7—7 of FIG. 6.

FIG. 8, a side view on line 8—8 of FIG. 6.

FIG. 9, an enlarged view showing details of the proximal end of the tourniquet tube.

FIG. 10, a view similar to FIG. 9 showing the suture ends secured.

FIG. 11, a face elevation showing a modified structure for suture retention.

FIG. 12, a view similar to FIG. 11 with a modified suture retention.

DETAILED DESCRIPTION OF THE INVENTION AND THE MANNER AND PROCESS OF USING IT

WITH REFERENCE TO THE DRAWINGS, in FIG. 1 a view of the heart organ 20 is depicted with a catheter 22 in place associated with a suitable tube 24. Adjacent to the catheter is a tourniquet tube 26. In FIG. 2, a purse string suture is illustrated as a series of in and out loops around the locus of the proposed catheter perforation. The two ends of the suture are shown at 30 and 32 loose at this point. A tourniquet tube or lumen 40 in FIG. 3 has a hook shaft 42 with a finger loop 44 at the proximal end and an elongate hook 46 at the distal end. The suture ends 30 and 32, which are actually longer than shown, are hooked on to the hook 46 and the shaft 42 is withdrawn from the lumen 40 which brings the ends 30 and 32 out to the distal end of the lumen as shown in FIG. 4.

These free ends are then wrapped around the neck portion 50 of a retaining button 52 and secured (FIG. 5A) in a slit or notch 54. Further details of the securing device are shown in FIGS. 6 to 10.

In FIGS. 6 and 7, the lumen 40 has an enlarged proximal head end 48 on one side of which is the neck or shank portion 50 and the button 52. FIG. 8 is a side elevation taken on line 8—8 of FIG. 6. An end view of the head of the lumen is shown in FIG. 7 where it will be seen that there is a modification wherein opposed slits 54 and 56 are cut into the annular rim and the side walls of the head with radiused corners to provide a smooth entry. When the sutures 30 and 32 are drawn from the distal end of the lumen up to and out of the proximal head end 48 as in FIG. 9, they can be grasped by the operator, brought down into the slit 54, wound around the shank 50 and locked behind the knob or button 52. Then the remaining ends may be brought back into the slit or notch 54 and across into the opposed slit 56 where they will be frictionally secured as in FIG. 10.

In FIGS. 11 and 12, a modified structure is illustrated. The shank 50 of the button or knob 52 is slit transversely in FIG. 10 behind the knob and up from the bottom to the dotted line 60 so that the sutures can be pulled into the slit 62 in the shank 50 and retained securely. In FIG. 12, two chordal slits are cut into the shank 50, one from the bottom and one from the top, to dotted lines 64 and 66, resepectively, providing retention slits 68 and 70. Thus, in this embodiment the sutures can be secured in the top or bottom slits or both.

The suture lumen 40 can then be tied to the catheter 22 (FIG. 1) after the catheter is installed in the heart wall. Thus, there is a mutual stabilization of the suture lumen and the catheter until the surgery is completed.

Upon completion of the surgery, the lumen 40 is released from the catheter and the catheter removed. The ends of the sutures can then be readily released from the notches 54, 56 and the head 48 and the button 50, the lumen 40 removed, and the sutures drawn tight to close the catheter opening, tied in a conventional manner, and clipped to leave the suture intact.

The above unit may be utilized with various suture materials such as silk, braided strands, or monofilament.

What is claimed is:

1. A suture lumen for securing sutures in a surgical procedure which comprises:
    (a) a lumen open at both ends and having a proximal end and a distal end, (b) a projection at one portion of said lumen adjacent the proximal end independent of the lumen passage having an annular recess to receive sutures wound into said recess, and (c) means forming a notch adjacent said projection to frictionally engage suture ends drawn into the notch.

2. A suture lumen as defined in claim 1 in which a head portion is formed at the proximal end of said lumen and said projection is mounted on said head portion and comprises a shank portion and a button on said shank portion.

3. A suture lumen as defined in claim 2 in which a transverse slit is formed in said shank behind said head portion to retain sutures wound around said shank and pulled into said slit.

4. A suture lumen as defined in claim 2 in which two transverse chordal slits are formed on said shank behind said head portion to retain sutures wound around said shank and pulled into one or more of said slits.

5. A suture lumen as defined in claim 1 in which a head portion is formed at the proximal end of said lumen having an annular rim provided with one or more notches to frictionally engage suture ends.

6. A suture lumen as defined in claim 1 in which a head portion is formed at the proximal end of said lumen having an annular rim coaxial with said lumen, said rim having one or more axial slits dimensioned to frictionally engage suture ends when drawn into a slit or slits.

7. A suture lumen as defined in claim 1 in which a head end is formed at the proximal end of the lumen having an open end surrounded by an annular rim having one or more slits to lock suture ends in frictional engagement, and a button on one side of said head portion adjacent a slit providing an annular recess to receive wound portions of said suture.

* * * * *